United States Patent [19]

Boehringer et al.

[11] Patent Number: 4,572,209

[45] Date of Patent: Feb. 25, 1986

[54] DYNAMIC BRAKED SPIROMETER

[75] Inventors: John R. Boehringer, Wynnewood; C. Harrison Williams, Wyncote, both of Pa.

[73] Assignee: Boehringer Laboratories, Wynnewood, Pa.

[21] Appl. No.: 412,226

[22] Filed: Aug. 27, 1982

[51] Int. Cl.[4] ............................................. A61B 5/08
[52] U.S. Cl. .................................. 128/726; 73/861.33; 73/861.81
[58] Field of Search ................... 128/725, 726; 272/99; 73/861.33, 861.81, 861.83, 861.87, 861.92, 861.79

[56] References Cited

U.S. PATENT DOCUMENTS

| | | | |
|---|---|---|---|
| 2,299,406 | 10/1942 | Potter | 73/861.92 X |
| 3,863,806 | 2/1975 | Risser, Jr. | 73/861.79 |
| 3,937,081 | 2/1976 | Dabanian et al. | 73/861.33 |
| 4,047,433 | 9/1977 | Dabanian | 73/861.33 |
| 4,182,175 | 1/1980 | Boehringer | 73/861.81 |

FOREIGN PATENT DOCUMENTS 0585845  12/1977  U.S.S.R. ............................ 128/726

Primary Examiner—Edward M. Coven
Attorney, Agent, or Firm—Paul & Paul

[57] ABSTRACT

An improved spirometer is disclosed which permits more accurate measurement of the volume of air exhaled from the lungs of a patient. The improvement comprises flow-responsive means such as a pair of vanes disposed downstream of the rotor. The vanes cause the air flow through the spirometer to stop, almost instantaneously, with the cessation of flow into the spirometer. Thus, after the patient stops exhaling through the spirometer, the rotor stops almost immediately, permitting more accurate measurements of the volume of air exhaled.

8 Claims, 4 Drawing Figures

DYNAMIC BRAKED SPIROMETER

BACKGROUND OF THE INVENTION

This invention relates to the field of spirometers. Spriometers have been known for some time as a means of measuring the volume of air exhaled by a patient. One type of spirometer is disclosed in U.S. Pat. No. 4,182,175, the disclosure of which is incorporated herein by reference.

In spirometers such as those described in the above-cited patent, there is provided a stator, and a rotor disposed within the stator. The stator has slots allowing air to enter from the periphery, and to cause the rotor to rotate. In spirometers of the type described, the flow of air sets up a vortex within the stator. The turbine rotor rides around with this vortex, and the speed, in rotations per minute (rpm) of the vortex is linearly proportional to the flow over a fairly wide range.

The problem with turbine systems of this kind is that the vortex generally continues to rotate somewhat after the air flow stops. Since the vortex is typically spinning at 30,000 to 60,000 rpm, there is considerable energy to dissipate. Without any flow, generated by the exhalation of the patient, to move the vortex into the exit tube of the spirometer, there is not much friction to stop the spinning. Thus, the rotor generally continues to turn somewhat after the patient ceases to exhale. The rotor is said to "coast." In the prior art, the only means of eliminating coasting has been to rely on friction of the mechanical gear train. However, when either a low friction gear train or an electronic or radiation beam type of rotation counter and/or flow measuring device is used, this coasting has made it impractical, in the prior art, to derive a really accurate reading of volume of air flow based on the number of turns of the rotor.

The present invention provides a structure which eliminates coasting, and thus makes it possible to measure the volume of air flow directly from the rotor. Since it is then practical to use a low-friction drive train or friction-free measuring device, it is possible to have an extremely sensitive spirometer, which responds to extremely low air flows.

SUMMARY OF THE INVENTION

The present invention solves the problems described above by providing flow-responsive braking means in the form of a pair of vanes disposed within the spirometer, downstream of the rotor. The vanes comprise a pair of flat plates, joined at right angles, and fixedly mounted within the spirometer housing. It is found that, when air is forced through the spirometer, such as when a patient exhales, the vanes do not interfere with the air flow. But when the patient ceases to exhale, and the flow stops, the vanes act to eliminate vortices, within the spirometer, causing the rotor to stop almost instantaneously with the cessation of air flow into the spirometer.

Accordingly, it is a primary object of the present invention to provide an improved spirometer which substantially eliminates coasting of the rotor.

It is a further object of the invention to provide a spirometer which permits extremely accurate measurement of volume of air flow, even when the flow is very small.

It is a further object of the present invention to provide an improvement for a spirometer which eliminates coasting of the rotor, but also which does not interfere with the operation of the spirometer when air is flowing through the device.

Other objects and advantages of the present invention will be apparent to those skilled in the art from a reading of the following brief description of the drawings, the detailed description of the invention, and the appended claims.

BRIEF DESCRIPTION OF THE DRAWINGS

FIG. 2 is a cross-sectional view, taken along the line 2—2 of FIG. 1.

FIG. 3 is a cross-sectional view, taken along the line 3—3 of FIG. 1.

DETAILED DESCRIPTION OF THE INVENTION

Figure 1:
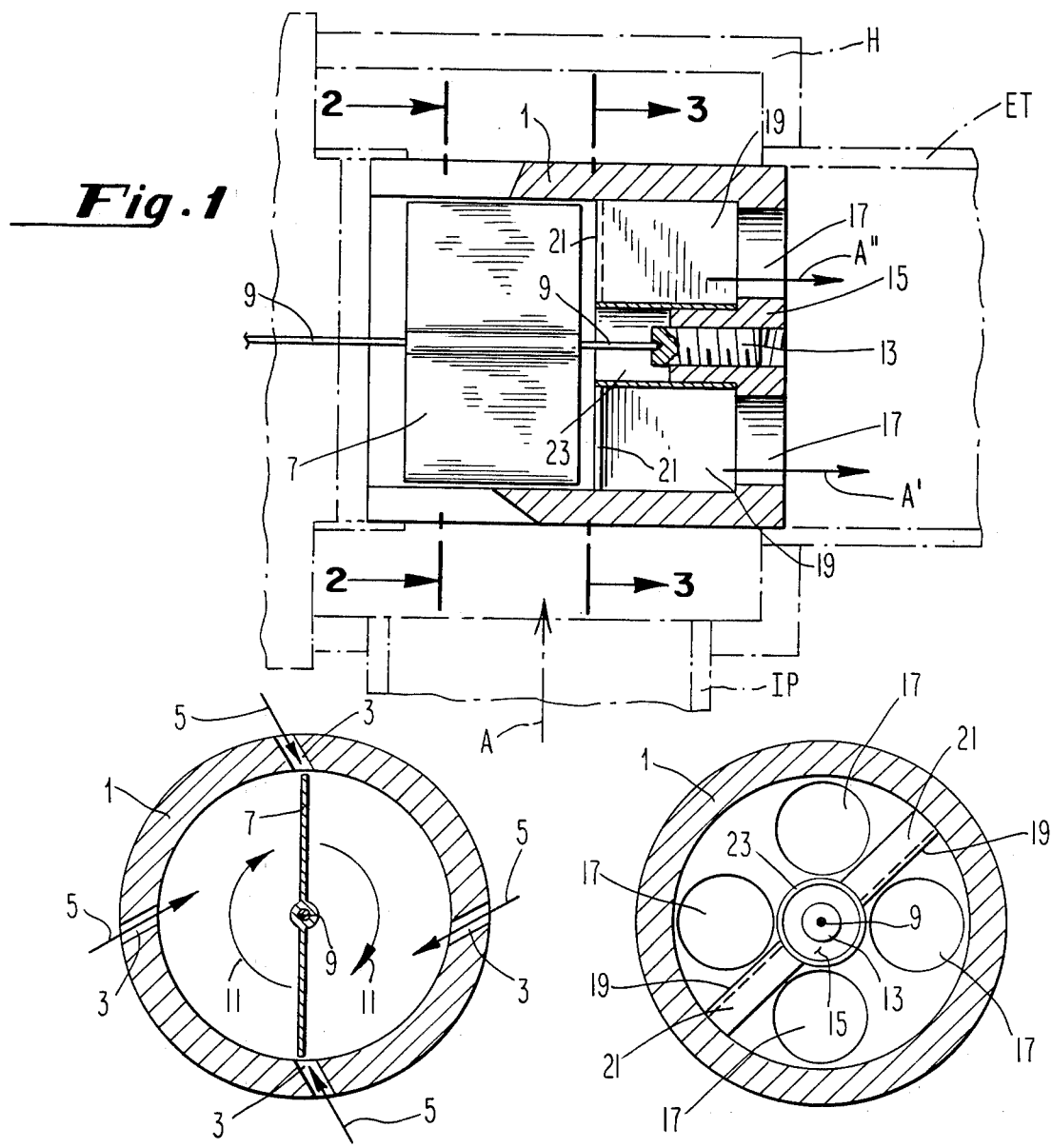
FIG. 1 is a cross-sectional view, partially in phantom of the improved spirometer showing the rotor and vanes.

The dynamic braked spirometer of the present invention is illustrated in FIGS. 1, 2 and 3. These figures show only the essential features of the present invention. It is understood that a suitable external housing and counter apparatus (shown in phantom) is to be provided, which may in fact be of types which are known in the art (as illustrated in the above-cited patent, or of other types to be later developed). In FIGS. 1 and 3, there is shown stator 1, the stator having a plurality of slots 3, through which air can enter in the direction indicated by arrows 5. The slots 3, in combination with housing means H (phantom) surrounding the stator, comprises an inlet port IP through which air exhaled by a patient can flow, into the spirometer, in the direction of arrow A.

Disposed within stator 1 is rotor 7. Rotor 7 may be composed of separate elements bonded together, as is described in the above-cited patent, or it may be integrally formed. The precise structure of the rotor is not relevant to the present invention. The rotor is mounted to rotate on shaft 9, as indicated by arrows 11. The combination of the rotor, stator, and drive shaft thus comprises a turbine means, similar to that shown in the cited patent.

Shaft 9 is seated for rotation in and relative to an axially adjustably positionable threaded bar 13, which is in threaded engagement within annulus 15. Holes 17 allow air to exit from the spirometer. These holes comprise part of the outlet port of the spirometer. In the embodiment illustrated, there are four holes 17, as shown in FIG. 3. The spirometer may be provided with an exit tube ET of the type illustrated in the cited patent.

Figure 4:
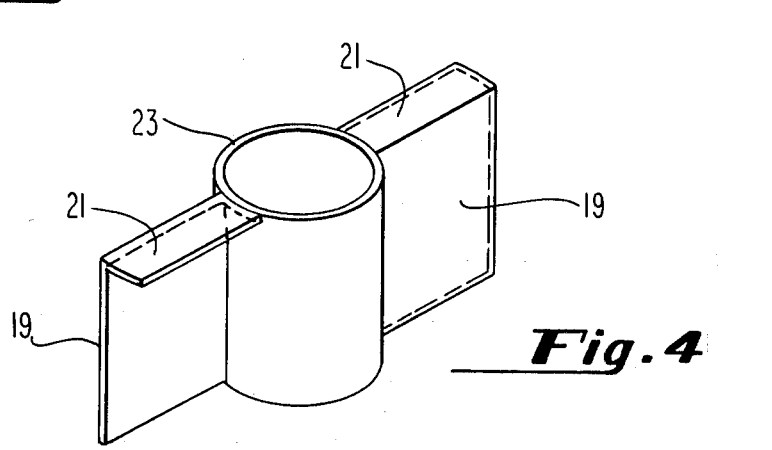
FIG. 4 is a perspective view, in isolation, of the pair of vanes used in the present invention.

The essential element of the present invention is the flow-responsive braking means. In a preferred embodiment, those means comprise a pair of vanes, shown in an isolated perspective view in FIG. 4, and shown also in FIGS. 1 and 3. Each vane comprises a pair of flat plates 19 and 21, joined at right angles to each other. The vanes are attached to a hollow cylinder 23. In the embodiment shown in the figures, the plates are of unequal areas, with the smaller plate of each pair defining a plane substantially perpendicular to the general direction of air flow through the spirometer (i.e. to the axis of the spirometer) and with the larger plate in each pair being parallel to the general direction of air flow.

As is shown in FIG. 3, the vanes are disposed so as not to interfere directly with the flow of air out of the spirometer, through holes 17. The vanes are fixedly mounted within the spirometer, in the position shown. It will be appreciated that the vanes in the embodiment shown are mounted downstream of the rotor. As used herein, the term "downstream" refers to the flow of air through the spirometer. The direction of flow, in FIG. 1, is generally from left to right, as per arrows A' and A".

It is understood that appropriate means are to be provided for connecting drive shaft 9 with sensing means for measuring the number of rotations, and converting that number into a reading of the volume of air passing through the spirometer. A means appropriate for this function is disclosed in the above-cited patent. Alternatively, an electronic counter or a radiant beam broken by rotation of the rotor can measure rotations for calculating flow.

The following is a description of the operation of the spirometer having vanes of the type described above. But it is to be understood that the theoretical basis for the present invention is not fully understood, and the invention is not to be limtied by the explanation suggested herein.

As stated above, it is believed that when air flows through the spirometer, vortices (rotational flow) form within the stator. When the flow stops, and in the absence of vanes, the vortices continue to circulate within the stator, and move in the downstream direction, enveloping the entire interior of the stator. The effect of the vanes appears to be to provide for impingement of rotational flow air thereon, to direct the flow of air in a direction opposite to that of the vortices. This effect results in a "cancellation" of the vortices, and the vortices are therefore braked to a sudden stop once the flow ceases.

While air from the patient is being forced through the spirometer, the vanes apparently have negligible effect on the flow. It appears that the flow in the region of the vanes is parallel to the vanes, and does not form a vortex. But when flow of air through the spirometer stops, the air in the region near the vanes tends to begin spinning, and rapidly reaches the speed of the vortex. But by virtue of the vanes, the flow of air is redirected against the vortex, and stops the vortex almost immediately. Since the vortex has stopped, the rotor has also stopped, and the number of turns of the rotor can be taken as an accurate measurement of the volume of air flowing through the spirometer.

The spirometer disclosed thus can be described as dynamically braked, because the braking of the rotor, after air flow stops, is accomplished by cancellation of two oppositely-directed streams of air.

When the present invention is used with a counter of the type disclosed in my above-mentioned patent, it is practical to use extremely low friction bearings for the drive shaft and obtain accurate coasting-free measurements, or to use an electronic pick-off device or broken beam device to convert the rotation of the rotor into an appropriate signal, also to yield accurate, coasting-free measurements. Because the problem of coasting is substantially eliminated, the number of turns of the drive shaft serves as a reliable indication of the volume of air flow. And because a low friction drive is used, the rotor, and hence the drive shaft, can turn in response to even the weakest of flows. Thus, not only does this invention allow more accurate determination of air flow, but it also provides a much more sensitive indicator than would have been possible in the prior art.

It is understood that many modifications are possible within the scope of the present invention. For example, the precise configuration of the inlet and outlet ports can be varied. The vanes themselves, which are a form of the essence of the present invention; namely the stopping means, may also be changed in various ways, such as by varying the number of the vanes, the angular relationships of the components, or by changing their area or configuration. All such modifications are to be deemed within the spirit and scope of the following claims.

What is claimed is:

1. In a spirometer having an inlet port, an outlet port, and rotational means disposed between said inlet and outlet ports and rotationally responsive to flow into said inlet port, the improvement comprising:

means, disposed in said spirometer for substantially instantaneously stopping the rotation of said rotational means in response to the cessation of flow into the inlet port, wherein said stopping means comprises flow impingement braking means for intersecting and stopping rotational flow of air in the spirometer that remains after cessation of flow into the inlet port, wherein said stopping means comprises at least one vane fixedly mounted within the spirometer, positioned so as not to directly interfere with the flow of air out of the spirometer, with said vane having at least a portion extending at least partially transverse to the direction of flow of air through the spirometer.

2. The improvement of claim 1, wherein said stopping means comprises two vanes.

3. In a spirometer having an inlet port, an outlet port, and rotational means disposed between said inlet and outlet ports and rotationally responsive to flow into said inlet port, the improvement comprising:

means, disposed in said spirometer for substantially instantaneously stopping the rotation of said rotational means in response to the cessation of flow into the inlet port, wherein said stopping means comprises two vanes, and wherein the vanes are fixedly mounted within the spirometer, and are positioned so as not to interfere with the flow of air out of the spirometer, wherein each vane comprises a pair of flat plates disposed substantially at right angles to each other.

4. The improvement of claim 3, wherein the plates have unequal areas.

5. The improvement of claim 4, wherein the smaller plate is disposed such that its surface defines a plane substantially perpendicular to the direction of flow of air out of the spirometer.

6. A spirometer comprising:
an inlet port,
an outlet port,
turbine means disposed between said inlet and outlet ports, and
at least one vane, the vane comprising a pair of flat plates disposed substantially at right angles to each other, wherein one of the plates defines a plane substantially perpendicular to the direction of air flow through the spirometer.

7. The spirometer of claim 6, wherein there are two vanes, the vanes being fixedly mounted within the spirometer.

8. A spirometer comprising a stator having a plurality of slots, the slots being adapted for entry of air into the spirometer, the stator having an axis therein, a rotor disposed within the spirometer, the rotor being mounted on a drive shaft, the drive shaft being oriented along the axis of the stator, a plurality of outlet holes, and at least one vane disposed within the stator, and located downstream of the rotor, each vane comprising of plate means, the vanes being fixedly mounted within the spirometer, and disposed in a position such that the vanes do not directly interfere with the flow of air out of the spirometer, with at least one said plate means of at least one said vane having at least a portion extending at least partially transverse to the direction of flow of air through the spirometer and comprising flow impingement braking means for intercepting and stopping rotational flow of air in the spirometer that remains after cessation of flow into the spirometer.

* * * * *